US010837974B2

(12) United States Patent
Postma et al.

(10) Patent No.: US 10,837,974 B2
(45) Date of Patent: Nov. 17, 2020

(54) SYSTEM, APPARATUS AND METHOD FOR AUTO-REPLENISHMENT AND MONITORING OF A MEDICAL INSTRUMENT

(75) Inventors: Stephen J. Postma, New Berlin, WI (US); Anne Tate, Draper, UT (US); Keith McElroy, St. Charles, IL (US); Chris Weinert, Merengo, IL (US)

(73) Assignee: SYSMEX CORPORATION, Kobe (JP)

( * ) Notice: Subject to any disclaimer, the term of this patent is extended or adjusted under 35 U.S.C. 154(b) by 486 days.

(21) Appl. No.: 12/750,386

(22) Filed: Mar. 30, 2010

(65) Prior Publication Data

US 2011/0246215 A1  Oct. 6, 2011

(51) Int. Cl.
*G01N 35/00* (2006.01)
*G06Q 10/08* (2012.01)
(Continued)

(52) U.S. Cl.
CPC ..... *G01N 35/00663* (2013.01); *G06Q 10/087* (2013.01); *G06Q 30/0641* (2013.01);
(Continued)

(58) Field of Classification Search
CPC ................ G06F 19/322; G06F 19/366; G01N 35/00663; G01N 2035/00881;
(Continued)

(56) References Cited

U.S. PATENT DOCUMENTS 6,757,714 B1  6/2004  Hansen
7,046,134 B2  5/2006  Hansen
(Continued)

FOREIGN PATENT DOCUMENTS

CN  101065754 A  10/2007
CN  101448723 A  6/2009
(Continued)

OTHER PUBLICATIONS

Matsuzaki et al. JP2002-350451. Machine translation.*
(Continued)

*Primary Examiner* — Russell S Glass
(74) *Attorney, Agent, or Firm* — Brinks Gilson & Lione

(57) ABSTRACT

A replenishment center connected to a plurality of analyzer systems each comprising at least one analyzer module which performs analysis using a replenishable item is disclosed. The replenishment center includes a receiver configured to receive operation information from at least one of the plurality of analyzer systems that relates to utilization of the replenishable item, a database configured to record the operation information in relation to the at least one of the plurality of analyzer systems, an inventory calculator configured to calculate and store in the database a remaining quantity of inventory of the replenishable item kept for the at least one of the plurality of analyzer systems, based on the operation information recorded in the database, and a suggested order generator configured to generate, when the calculated remaining quantity becomes less than a predetermined threshold, a suggested order programmed to give a user of the at least one of the plurality of analyzer systems an option of accepting or rejecting the suggested order.

17 Claims, 12 Drawing Sheets

(51) Int. Cl.
  *G06Q 30/06* (2012.01)
  *G06Q 50/22* (2018.01)
  *G16H 10/60* (2018.01)
  *G16H 10/40* (2018.01)

(52) U.S. Cl.
  CPC ............. *G06Q 50/22* (2013.01); *G16H 10/40* (2018.01); *G16H 10/60* (2018.01); *G01N 2035/00881* (2013.01)

(58) Field of Classification Search
  CPC .. G06Q 30/0641; G06Q 10/087; G06Q 50/22; G16H 10/40; G16H 10/60
  See application file for complete search history.

(56) References Cited

U.S. PATENT DOCUMENTS

| | | | |
|---|---|---|---|
| 7,082,460 | B2 | 7/2006 | Hansen et al. |
| 7,117,239 | B1 | 10/2006 | Hansen |
| 7,149,792 | B1 | 12/2006 | Hansen et al. |
| 7,178,149 | B2 | 2/2007 | Hansen |
| 7,185,014 | B1 | 2/2007 | Hansen |
| 8,325,036 | B1 * | 12/2012 | Fuhr .................. G06Q 10/087 340/5.92 |
| 8,626,342 | B2 | 1/2014 | Williams, Jr. et al. |
| 2002/0010659 | A1 | 1/2002 | Cruse et al. |
| 2002/0082957 | A1 * | 6/2002 | Krassi ............... 705/29 |
| 2002/0107642 | A1 | 8/2002 | Nishida et al. |
| 2003/0088442 | A1 * | 5/2003 | Michael et al. .......... 705/3 |
| 2003/0158794 | A1 | 8/2003 | Harada et al. |
| 2006/0168005 | A1 | 7/2006 | Kanbara et al. |
| 2009/0134978 | A1 | 5/2009 | Imai |
| 2009/0281930 | A1 * | 11/2009 | Sakagami .............. 705/28 |
| 2010/0082483 | A1 * | 4/2010 | Sanders ............ G06Q 10/087 705/42 |
| 2010/0161345 | A1 * | 6/2010 | Cain et al. ................ 705/2 |

FOREIGN PATENT DOCUMENTS

| | | |
|---|---|---|
| EP | 2 022 737 A1 | 2/2009 |
| EP | 1 231 471 B1 | 4/2010 |
| JP | 2001-290975 A | 10/2001 |
| JP | 2002-157222 A | 5/2002 |
| JP | 2002-228667 A | 8/2002 |
| JP | 2002350451 | 12/2002 |
| JP | 2003248005 | 9/2003 |
| JP | 2003-344422 A | 12/2003 |
| JP | 2004-310143 A | 11/2004 |
| JP | 2005-18742 A | 1/2005 |
| JP | 2005-195401 A | 7/2005 |
| JP | 2006-221285 A | 8/2006 |
| JP | 2007314327 | 12/2007 |
| JP | 2008-180640 A | 8/2008 |
| WO | WO 01/93142 A1 | 12/2001 |
| WO | WO 02/10919 A2 | 2/2002 |
| WO | WO 03/090119 A1 | 10/2003 |
| WO | WO 2008/090888 A1 | 7/2008 |
| WO | WO 2010/074781 A2 | 7/2010 |

OTHER PUBLICATIONS

Ross, David. "Distribution Planning and Control" 1996. Chapman & Hall. Chapter 7., pp. 263-319.*
Office Action from Chinese Application No. 201110078373.7, dated Feb. 20, 2014, 15 pages.
Japanese Search Report with English translation, dated Jul. 15, 2014, pp. 1-20, issued in Japanese Patent Application No. 2011-035877, Japanese Patent Office, Tokyo, Japan.
Japanese Notice of Reasons for Refusal with English translation, dated Aug. 8, 2014, pp. 1-14, issued in Japanese Patent Application No. 2011-035877, Japanese Patent Office, Tokyo, Japan.
Japanese Written Opinion with English translation, dated Oct. 8, 2014, pp. 1-22, issued in Japanese Patent Application No. 2011-035877, Japanese Patent Office, Tokyo, Japan.
Japanese Decision to Grant with English translation, dated Mar. 13, 2015, pp. 1-5, issued in Japanese Patent Application No. 2011-035877, Japanese Patent Office, Tokyo, Japan.
Japanese Search Report with English translation, Jan. 15, 2016, pp. 1-33, issued in Japanese Patent Application No. 2015-088122, Japanese Patent Office, Tokyo, Japan.
Japanese Decision to Grant with English translation, dated Mar. 18, 2016, pp. 1-5, issued in Japanese Patent Application No. 2015-088122, Japanese Patent Office, Tokyo, Japan.
Japanese Search Report with English translation, dated Jan. 12, 2016, pp. 1-40, issued in Japanese Patent Application No. 2015-088121, Japanese Patent Office, Tokyo, Japan.
Japanese Notice of Reasons for Refusal with English translation, dated Feb. 19, 2016, pp. 1-10, issued in Japanese Patent Application No. 2015-088121, Japanese Patent Office, Tokyo, Japan.
Japanese Written Opinion with English translation, dated Apr. 15, 2016, pp. 1-35, issued in Japanese Patent Application No. 2015-088121, Japanese Patent Office, Tokyo, Japan.
Japanese Decision to Grant with English translation, dated Sep. 26, 2016, pp. 1-5, issued in Japanese Patent Application No. 2015-088121, Japanese Patent Office, Tokyo, Japan.
Chinese First Search, dated May 27, 2013, pp. 1, issued in Chinese Patent Application No. 2011-100783737, Chinese National Intellectual Property Association, Beijing, China.
Chinese First Office Action with English translation, dated Jun. 4, 2013, pp. 1-12, issued in Chinese Patent Application No. 2011-100783737, Chinese National Intellectual Property Association, Beijing, China.
Chinese Supplemental Search, dated Oct. 15, 2014, pp. 1, issued in Chinese Patent Application No. 2011-100783737, Chinese National Intellectual Property Association, Beijing, China.
Chinese Third Office Action with English translation, dated Oct. 27, 2014, pp. 1-19, issued in Chinese Patent Application No. 2011-100783737, Chinese National Intellectual Property Association, Beijing, China.
Chinese Fourth Office Action with English translation, dated May 6, 2014, pp. 1- 20, issued in Chinese Patent Application No. 2011-100783737, Chinese National Intellectual Property Association, Beijing, China.
Chinese Notice of Grant with English translation, dated Dec. 18, 2015, pp. 1-3, issued in Chinese Patent Application No. 2011-100783737, Chinese National Intellectual Property Association, Beijing, China.
European Extended Search Report, dated Feb. 20, 2014, pp. 1-5, issued in European Patent application No. 11156958.8, European Patent Office, Munich, Germany.
European Office Action, dated May 18, 2018, pp. 1-6, issued in European Patent application No. 11156958.8, European Patent Office, Munich, Germany.
European Summons to Oral Proceedings, dated Jun. 4, 2019, pp. 1-8, issued in European Patent application No. 11156958.8, European Patent Office, Munich, Germany.
Decision to Refuse a European Patent Application, dated Jan. 30, 2020, pp. 1-12, issued in European Patent Application No. 11156958.8, European Patent Office, Munich, Germany.

* cited by examiner

| | | | |
|---|---|---|---|
| Review Order | Adjust Stock | Reports | User Guide |

| SKU | Description | Recommended Quantity | Adjust Actual Quantity |
|---|---|---|---|
| PK-30L | CELLPACK, 20L | 0 | - [0] + |
| 054-0501-8 | CELLSHEATH C 20L | 0 | - [0] + |
| SE-90L | CELLSHEATH, 20L | 0 | - [0] + |
| RED-700A | RET-SEARCH II | 0 | - [0] + |
| FFD-200A | STROMATOLYSER 4DL | 8 | - [8] + |
| FFS-800A | STROMATOLYSER 4DS | 0 | - [0] + |
| FBA-200A | STROMATOLYSER FB, 5L | 0 | - [0] + |
| SNR-700A | STROMATOLYSER NR, 1L X 12ML | 0 | - [0] + |
| SIM-220A | STROMATOLYSER-IM, 10L | 8 | - [8] + |
| 064-2881-5 | Stromatolyser-NR(L) 3.6L Lyse | 5 | - [5] + |
| 064-2891-2 | Stromatolyser-NR(S) 3x43ml Di | 5 | - [5] + |
| SLS-210A | SULFOLYSER REAGENT, 3 X 500 | 0 | - [0] + |
| SLS-220A | SULFOLYSER, 5L | 2 | - [2] + |

Comments (200 char max):

PO Number:
57150-2080000040    (Check to save this PO as your default)

Reject Order    Submit Order

FIG. 7B

| | | | | |
|---|---|---|---|---|
| Review Order | Adjust Stock (714) | Reports | | |
| SKU (702) | Lot Number | Lot Expiration | Amount (718) | ☑ Show zero-quantity items (720) |
| 054-0501-8 | C8025 | 12/02/2009 | 0 | Edit |
| 064-2881-5 | A8010 | 11/28/2009 | 2 | Edit |
| 064-2881-5 | A9001 | 02/07/2010 | 3 | Edit |
| 064-2881-5 | A9002 | 03/11/2010 | 2 | Edit |
| 064-2891-2 | A8022 | 10/15/2009 | 3 | Edit |
| 064-2891-2 | A9007 | 02/26/2010 | 1 | Edit |
| 064-2891-2 | A9008 | 03/05/2010 | 1 | Edit (716) |
| 161-6002-0 | 110897 | 10/01/2009 | 9 | Edit |
| FBA-200A | C8018 | 06/09/2009 | 0 | Edit |
| FBA-200A | C8029 | 07/18/2009 | 0 | Edit |

1 2 3 4 5 6 7 8

These quantities reflect your existing stock + any items that are in transit.

FIG. 7C

| | | 724 728 722 726 732 | | |
|---|---|---|---|---|
| Review Order | Adjust Stock | Reports | | User Guide |

ORDER HISTORY ▽ Select a report to view

| Order ID | Status | PO | Modified Date | Modified By |
|---|---|---|---|---|
| 72 | Rejected | 57150-2080000040 | 9/29/2009 1:35:22 PM | Ricardo Chapa |
| 62 | Delivered | 57150-2080000040 | 9/9/2009 4:25:22 PM | Ricardo Chapa |
| 59 | Delivered | 57150-2080000040 | 8/19/2009 12:13:15 PM | Angela Garrett |
| 58 | Delivered | 57150-2080000040 | 8/12/2009 3:28:15 PM | Ricardo Chapa |
| 53 | Modified/ Delivered | 57150-2080000040 | 7/27/2009 8:13:51 AM | Emily Cederlund |

1 2

ORDER DETAILS

| SKU | Description | Quantity | Confirmed Quantity |
|---|---|---|---|
| FFD-200A | STROMATOLYSER 4DL | 0 | 4 |
| FFS-800A | STROMATOLYSER 4DS | 0 | 2 |
| FBA-200A | STROMATOLYSER FB, 5L | 78 | 5 |

Comments:
Reduced FBA order, added FFD and FFS as inventory is down to 1 box each.

730

Tracking numbers
1ZW271F70359192575
1ZW271F70359209413
1ZW271F70359330639
1ZW271F70359467395
1ZW271F70359690625
1ZW271F70360143008
1ZW271F70360193446

FIG. 7D

SYSTEM, APPARATUS AND METHOD FOR AUTO-REPLENISHMENT AND MONITORING OF A MEDICAL INSTRUMENT

BACKGROUND

Medical devices and instruments such as, for example, XE-Series Automated Hematology Analyzers designed, manufactured and marketed by Sysmex Corporation®, utilize one or more reagents and other consumable or replenishable items to test and evaluate patient samples. In laboratory environments, these medical devices and instruments are utilized to process a high volume of samples received from many different sources and locations. For example, one medical device may be utilized in a hospital laboratory to process testing and samples from patients of the hospital. In another example, one or more medical devices or instruments may be utilized in an independent laboratory that receives and tests samples from numerous hospitals, clinics or other sources. In order to ensure full or optimal utilization of the medical devices, a continuous supply of the one or more reagents and other consumable or replenishable items must be available for the testing and evaluation of the patient samples of interest.

U.S. Patent Application Publication No. 2002/0107642, titled "Method and Apparatus for Managing Consumer Goods Used in an Analyzer". The application discloses a method and apparatus which manage consumer goods used in an analyzer and prevent order loss from occurring due to an analyzer user's human error. In the method, consumption status of consumer goods consumed by an analyzer is monitored and analyzed according to consumer goods in which said consumer goods suppliers deal. The analyzed consumer goods consumption status and supply management information are transmitted to a management unit for the analyzer, consumer goods suppliers' supply management units or a supply management unit for a consumer goods vendor. Supply status is confirmed based on the consumer goods supply management information. Payment is requested from an analyzer administrator, consumer goods suppliers or a consumer goods vendor in consideration of use of the information based on said step that monitors consumer goods consumption status and said step that analyzes the consumer goods consumption status.

U.S. Patent Application Publication No. 2009/00134978, titled "Stock Article Management System". The application discloses that an automatic analyzer transmits information about stock articles used in automatic analyzers provided in a plurality of facilities, respectively, to a management station through a network. The management station manages the stock articles in the plurality of facilities. Each facility includes an information exchanger on which stock articles each appended with an RFID tag are arranged; a first reader/writer exchanging, with the RFID tag, information about the stock articles, when the stock articles are arranged on the information exchanger; a second reader/writer provided in the automatic analyzer, wherein the second reader/writer exchanges, with the RFID tag, information about the stock articles, shares, with the first reader/writer, the information about the stock articles, when the stock articles are mounted on the automatic analyzer; and a processor that processes the information about the stock articles. The management station collectively manages in real time the stock articles in the facilities.

Japanese Patent Application Publication No. 2003-248005 discloses an analyzer that sends reagent information to a reagent supplier via a network. The reagent supplier prepares and sends a reagent shipping list, based on the received reagent information.

Japanese Patent Application Publication No. 2002-350451 discloses an analyzer that sends reagent information to a reagent supplier via a network. Based on the received reagent information, the reagent supplier predicts future consumption of reagents by a user and sends an order to its reagent vender, based on the prediction.

In each of the above-identified U.S. and Japanese patent records, the user of the system or device has no control over the ordering of reagent supplies.

It would be desirable to improve on each of these known systems and methods to decrease the monitoring and management activities necessary to efficiently utilize the medical devices and instruments and manage the one or more reagents, consumables or replenishable items. Moreover, it would be desirable to streamline the management and replenishment of the one or more reagents and other consumable or replenishable items.

SUMMARY

The disclosed system, apparatus and method relates to an auto-replenishment system that provides a mechanism by which medical devices may be configured to monitor, communicate and automatically reorder one or more reagents and other consumable or replenishable items.

In an embodiment, a replenishment center connected to a plurality of analyzer systems each comprising at least one analyzer module which performs analysis using a replenishable item is disclosed. The replenishment center includes a receiver configured to receive operation information from at least one of the plurality of analyzer systems, wherein the operation information relates to utilization of the replenishable item, a database configured to record the operation information in relation to the at least one of the plurality of analyzer systems, an inventory calculator configured to calculate and store in the database a remaining quantity of inventory of the replenishable item kept for the at least one of the plurality of analyzer systems, based on the operation information recorded in the database, and a suggested order generator configured to generate, when the calculated remaining quantity becomes less than a predetermined threshold, a suggested order programmed to give a user of the at least one of the plurality of analyzer systems an option of accepting or rejecting the suggested order.

In another embodiment, a method for soliciting an order of a replenishable item from a plurality of analyzer systems each comprising at least one analyzer module which performs analysis using the replenishable item is disclosed. The method includes receiving operation information from at least one of the plurality of analyzer systems which relates to consumption of the replenishable item, recording in a database the operation information in relation to the at least one of the plurality of analyzer systems, calculating and store in the database a remaining quantity of inventory of the replenishable item kept for the plurality of analyzer systems, based on the operation information recorded in the database, and generating, when the calculated remaining quantity becomes less than a predetermined threshold, a suggested order programmed to give a user of the analyzer system an option of accepting or rejecting the suggested order.

In another embodiment, an analyzer system is disclosed. The analyzer includes an analysis module utilizing a replenishable item to analyze a sample, a tracking module configured to monitor analysis operations of the analysis module and create operation information indicative of the analysis operations of the analysis module, wherein the operation information relates to consumption of the replenishable item, a transmitter configured to transmit the operation information to a replenishment center, and an order presenter configured to present a suggested order in such a way as to give a user of the system an option of accepting or rejecting the suggested order.

In another embodiment, a method for giving a user of an analyzer system an option on an order for a replenishable item used in the analyzer system is disclosed. The method includes utilizing the replenishable item during the analysis of a sample, monitoring analysis operations and creating operation information indicative of the analysis operations, wherein the operation information relates to consumption of the replenishable item, transmitting the operation information to a replenishment center, receiving a suggested order for ordering the replenishable item from the replenishment center, and providing the received suggested order to the user of the analyzer system with an option of accepting or rejecting the suggested order.

In another embodiment, a system for auto-replenishment and monitoring is disclosed. The system includes an analyzer system disposed at a first location and connected to a network, wherein the analyzer system further includes an analysis module using a replenishable item to analyze a sample, a tracking module configured to monitor analysis operations of the analysis module and create operation information indicative of the analysis operations of the analysis module, wherein the operation information relates to consumption of the replenishable item, and a transmitter configured to transmit the operation information to a network. The system further includes a replenishment center disposed at a second location and connected to the network, wherein the replenishment center includes a receiver configured to receive operation information from an analyzer system which relates to consumption of the replenishable item, a database configured to record the operation information in relation to the at least one analyzer system, an inventory calculator configured to calculate and store in the database a remaining quantity of inventory of the replenishable item kept for the analyzer system, based on the operation information recorded in the database, and a suggested order generator configured to generate, when the calculated remaining quantity becomes less than a predetermined threshold, a suggested order programmed to give a user of the analyzer system an option of accepting or rejecting the suggested order.

Other embodiments are disclosed, and each of the embodiments can be used alone or together in combination. Additional features and advantages of the disclosed embodiments are described in, and will be apparent from, the following Detailed Description and the figures.

BRIEF DESCRIPTION OF THE FIGURES

FIGS. 7A to 7E illustrate exemplary interface screens that may be utilized in connection with an exemplary auto-replenishment and monitoring system.

DETAILED DESCRIPTION

Figure 1:
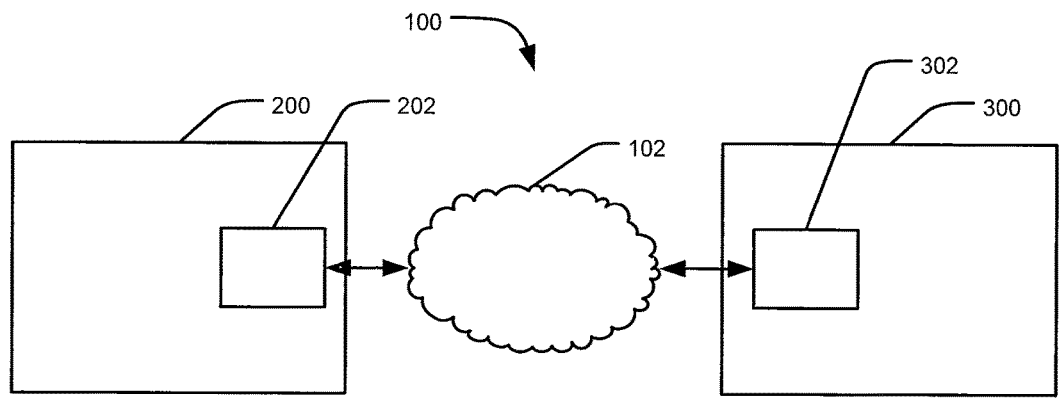
FIG. 1 illustrates an embodiment of a system for auto-replenishment and monitoring as disclosed herein.

The system, apparatus and method disclosed herein are configured to provide an efficient process by which by which medical devices may be configured to monitor, communicate and automatically reorder one or more reagents and other consumable or replenishable items. In particular, the disclosure provides an efficient ordering process, a way to manage a customer or user's on-site inventory of reagents, consumables and other replenishable items, and reduces or eliminates the need for expedited shipping reagents, consumables and other replenishable items to may arise from the inefficient inventory control mechanisms utilized in known/current asset management systems.

In order to maximize the utilization and throughput of medical devices such as a hematology device or other blood analysis equipment, a constant, available supply of reagents and other consumable or replenishable items must be ensured. If a customer or other user of, for example, a hematology device insufficiently stocks or otherwise runs out of reagents or other consumable materials, the medical device can be rendered non-functional until replacements can be procured. Rush procurement of reagents and other consumable or replenishable items can be a costly and time-consuming endeavor. Moreover, reagents and other consumable materials used for analysis in medical devices are often viable for limited periods. Large inventories of reagents and other consumable or replenishable materials may result in waste and disposal of unused inventories after their expiration dates. Customers or other users of the exemplary medical devices such as a hematology device or other blood analysis equipment often lack the personnel, inventory tracking resources and/or system monitoring tools to detect and address when a low inventory situation is about to occur. The disclosed system, apparatus and method addresses the shortcoming noted above and provides numerous additional benefits.

Additional benefits realized by the disclosed system, apparatus and method include an ability to: accurately deduce replenishable item usage patterns; forecast replenishable item production requirements based on usage patterns; reduce shipping costs associated with expedited shipping and processing of replenishable items; reduce inventory management costs; and improve or enhance the overall utilization or "up-time" of the medical devices being monitored.

In one embodiment, the disclosed system, apparatus and method may be configured to track and determine, based on medical device identifier such as a machine or model serial number, a number of reagent or consumable cycles, reagent or consumable container usage, a correlation between reagent or consumable cycles and reagent or consumable container usage, and identify the reagent or consumable products or items depleted and necessary to continued efficient operation of the medical device and/r hematology device. The gathered information may, in turn, be communicated via the medical device and/or hematology device to a replenishment center for order and fulfillment of the depleted reagent or consumable items.

FIG. 1 illustrates one embodiment of an auto-replenishment system 100 constructed in accordance with the disclosure provided herein. The auto-replenishment system 100, in this exemplary embodiment, includes a medical device 200 in communication with a replenishment center 300 via communications network or link 102. The medical device 200 may be, for example, an XE-Series Automated Hematology Analyzers designed, manufactured and marketed by Sysmex Corporation®. As used herein, the term medical device is intended to be synonymous with the terms "hematology device", "medical instrument", "medical analysis device" and all other reasonable descriptions for a device utilizes reagents and other consumable or replenishable items in a medical or laboratory operation. The medical device 200 may include a communication agent or more specifically a device communication agent 202. The device communication agent 202 may be any hardware or software module such as a transmitter and/or receiver configured to facilitate communication. For example, the device communication agent 202 may be provided by Axeda Corporation based on technology developed by the Questra Corporation and may enable communications between the medical device 200 and the communications link 102. The communications link 102 may incorporate the Internet, a virtual private network (VPN), a wide area network (WAN), a public switched telephone network (PSTN) or any other known or foreseeable communications medium.

The communications link 102 may, in turn, connect the medical device 102 to the replenishment center 300 via a replenishment communication agent 302. The replenishment communication agent 302 may, similar to the device communication agent 202, be any hardware or software module configured to facilitate communication. The replenishment center 300 may be any known back office, order processing, material storage and/or order fulfillment center or combination thereof.

Figure 2:
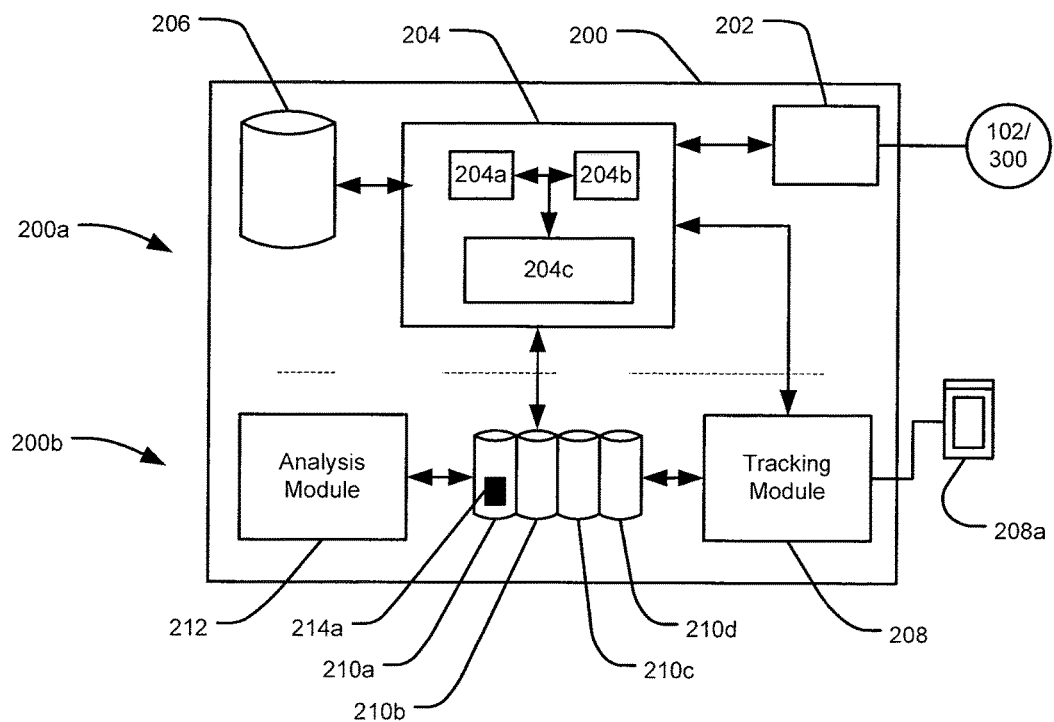
FIG. 2 illustrates a block diagram representative of a medical device configured according to the disclosure provided herein.

FIG. 2 illustrates a detailed block diagram of the medical device 200 including the components, subsystems, elements and modules relevant and/or utilized in connection with the auto-replenishment system 100. In this exemplary embodiment, the medical device 200 is shown to include a replenishment subsystem 200a and an analysis subsystem 200b. It will be understood that the subsystems 200a and 200b have been identified and/or designated to aid in the explanation and understanding of the auto-replenishment system 100 and is not intended to limit scope and configuration thereof. While these subsystems 200a and 200b are shown as components or elements of the medical device 200, they may, in alternative embodiments, be physically separate systems or subsystems in communication with each other.

The replenishment subsystem 200a, in this exemplary embodiment, includes the device communication agent 202 in communication with a control module 204 and a database 206. The control module 204 may include a processor 204a communicatively coupled to a memory 204b. The memory 204b may be any known or contemplated volatile or non-volatile storage medium (e.g., RAM, ROM, a solid state hard drive (SSD), a hard drive (HD), and an optical drive) configured to store program logic and/or computer readable instructions. The processor 204a may be any general or specific circuit or controller configured to execute or run the program logic or instructions stored in the memory 204b. The processor 204a and the memory 204b may cooperate to generate and present a graphical user interface (GUI) 204c to a user of the medical device 200. The GUI 204c may provide the user access to the replenishment subsystem 200a, analysis subsystem 200b and the replenishment center 300 (see FIGS. 1 and 3) via the communication link 102.

The replenishment subsystem 200a may, in this exemplary embodiment, include a database 206 configured to store data or information relating to the reagents and other consumable or replenishable items utilized in a medical or laboratory operation. For example, the database 206 may searchably store information or data related to: reagent and/or quality control identifiers; reagent and/or quality control lot identifiers or number; reagent expiration dates, reagent load dates, operational history data; troubleshooting data; and communication logs or data. The database 206 may further be in communication, via the control module 204, with a tracking module 208 within the analysis subsystem 200b.

The tracking module 208 may include both hardware and software necessary to gather, organize and monitor the reagent and quality control information and identifiers stored in the database 206. For example, the tracking module 108 may include a scanner 208a configured to read product information via a barcode associated with each of the reagents or other consumables generally identified by the reference numerals 210a to 210d. Alternatively, the scanner 208a may be configured to receive product information contained on a radio frequency identification (RFID) tag associated with each of the reagents or other consumables 210a to 210d. The tracking module 208 may further store cycle and procedure use information received from an analysis module 212. Alternatively, the analysis module 212 may communicate or copy information directly to the database 206 and/or the control module 204.

The analysis module 212 may be fluidly coupled as well as communicatively coupled to the reagents or other consumables 210a to 210d. The analysis module 212 may include the instruments, components, analysis and controls systems necessary to test and analyze patient samples. For example, the medical device 200 may be a hematology device such as an XE-series hematology diagnostic device. In this case, the analysis module 212 may include a semiconductive laser, cell specific lyse and fluorescent flow cytometry components, platelet preparation and control components. Other device configurations and/or analysis capabilities may require different components.

The analysis module 212 may further include one or more printers or storage device to saved and report analysis results. Moreover, the analysis module 212 may record locally, or communicate to, for example, the database 206 or the control module 204, the number of operation or testing cycles performed by the analysis module 212. As used herein, operation or testing cycles and information includes any functions, sample analyses, cleaning and maintenance activities that deplete or otherwise consume reagents or other replenishable items 210a to 210d. In another embodiment, the reagents or other replenishable items 210a to 210d may be monitored, weighed or otherwise measured to directly determine the amounts of each is consumed or utilized during the operation or testing cycles of the medical device 200.

The gathered operation information relating to the testing or operational cycles performed by the analysis module 212 may be communicated and/or stored by the database 206 and control module 204. Moreover, the gathered operation information relating to the testing or operational cycles performed by the analysis module 212 may be combined and correlated with the product information stored in the database 206. Because the amount of each reagent or other replenishable item 210a to 212d is known for each test or analysis performed by the analysis module 212, the combined and correlated data may be analyzed to determine how much of each reagent or other replenishable item 210a to 212d remains.

The combined and correlated data can further be analyzed to determine how long the reagents or other replenishable items 210a to 212d have been loaded onto the medical device 200 and whether or not they are within their expiration periods. The combined and correlated information and/or the operation information may be provided to the device communication agent 202 or transmitter for transmission to the replenishment center 300 and receiver or replenishment communication agent 302 via the communication link 102. Transmission to the replenishment center 300 may be pushed from the medical device 200 or pulled from the replenishment center 300 at regular intervals or upon occurrence of one or more predefined triggers or flags. For example, the replenishment center 300 may request the combined and correlated data from the medical device 200 on a regular (e.g., daily, hourly) schedule. Inversely, the medical device 200 may provide the combined and correlated data to the replenishment center 300 on a regular (e.g., daily, hourly) schedule during, for example, a predefined working period. The combined and correlated data and/or operation information may be provided in an uncompressed, compressed and/or encrypted format.

In operation, the user of the medical device 200 may at startup or at the prompting of the GUI 204c, load one or more reagents or other replenishable items 210a to 210d. For example, the user may utilize the scanner 208a to scan or read a barcode 214a associated with the replenishable item 110a. The scanned information may be communicated to the database 206 for storage and to the control module 204 for display via the GUI 204c. The user may visually verify that the scanned and presented data matches the data on the replenishable item 110a. Alternatively, the GUI 204c may require the user to record and affirm the data by pressing an ACCEPT button or other graphical or text indication. The scanned information may further be communicated to the analysis module 212 for use in the operation or testing cycles. The scanned information may further include location or position information at which replenishable item 210a is coupled to the analysis module 212.

Figure 3:
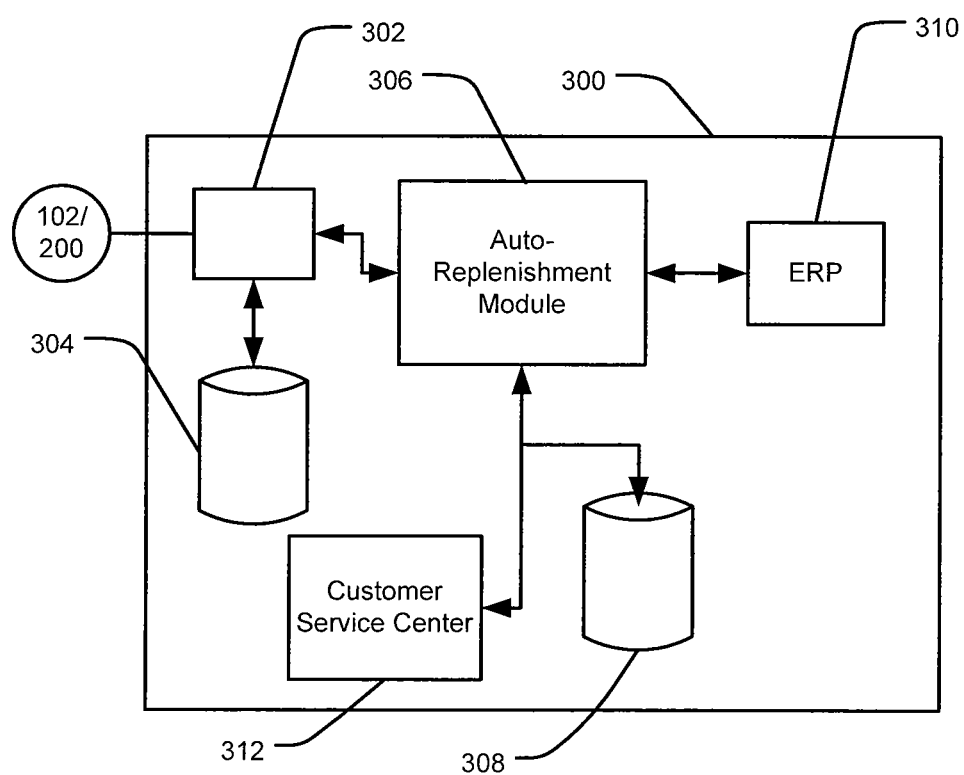
FIG. 3 illustrated a block diagram representative of a replenishment center configured according to the disclosure provided herein.

FIG. 3 illustrates a detailed block diagram of the replenishment center 300 including the components, subsystems, databases and modules utilized in connection with the auto-replenishment system 100. The replenishment communication agent 302, as previously discussed, is in communication with the device communication agent 202 and may be a transmitter and receiver configured to receive and/or request the combined and correlated data from the medical device 200. The replenishment communication agent 302 may include or be in communication with a communication database 304. The communication database 304 may store the communication or information request schedule associated with the medical device 200. The communication database 304 may further include device identifiers such machine serial number, secure internet protocol address, location information or identifiers or any other alias information utilized to uniquely identify the medical device 200.

The transmitter and receiver portions of the replenishment communication agent 302 may further be in communication with an auto-replenishment module 306. The auto-replenishment module 306, as with the control module 204, includes the memory and processing capabilities necessary to store, analyze and manipulate the received the combined and correlated data. For example, the auto-replenishment module 306 may include the logic and algorithms to unencrypt and/or decompress the received combined and correlated data. If required, the received the combined and correlated data may be parsed or otherwise manipulated to return it to a usable format.

The auto-replenishment module 306 may further communicate with an auto-replenishment database 308. The auto-replacement database 308 may store the details of a service agreement between the user of the medical device 200 and the replenishment center 300. For example, the auto-replenishment database 308 may include shipping addresses to which the replenishable items 210a to 212d are delivered; purchase orders to be referenced in any given replenishment order, order history details, maximum credit or charge information, minimum supply thresholds based on previous orders and/or direct query of a customer's stock system (if allowed). The auto-replenishment module 306 may receive via the receiver portion of the replenishment communication agent 302 the combined and correlated data and/or operation information from the medical device 200. The auto-replenishment database 308 may, in turn, utilize a record adjustor and/or updater to store the received operation information. The auto-replenishment module 306 and the auto-replenishment database 308 may further include an inventory calculator to determine, based on the known and type of operating cycles performed by the medical device 200, whether the replenishable item 210a has or will be exhausted in the near future. The auto-replenishment database 308 and the auto-replenishment module 306 may further utilize an alert sender to generate and communicate alerts to the medical device 200 if the user attempts to load and/or utilize a replenishable item that has passed an expiration date.

The auto-replenishment module 306 may query an enterprise resource planning (ERP) module 310 and utilize the inventory calculator to determine, based on order histories, whether a replacement replenishable item 210a is available to the user. If a replacement replenishable item 210a is available, the records of replenishment center 300 may be updated utilizing the record updater to reflect the change in status. If a replacement replenishable item 210a is not available, the ERP system 310 or other suggested order generator may automatically generate a proposed purchase and shipping order to supply a replacement replenishable item 210a to the user. For example, if it is determined by the auto-replenishment module 306 that the stock level of the replenishable item 210a falls below a predefined threshold stored in the auto-replenishment database 308, the replenishment center 300 may access the suggested order generator or subroutine to automatically generate a proposed purchase and shipping order to supply a replacement replenishable item 210a to the user. In this way, the order may be sent directly to the medical device 200 for approval and/or acknowledgement by the user.

In another embodiment, a determination by the auto-replenishment module 306 and/or the inventory calculator that the stock level of the replenishable item 210a falls below a predefined threshold may trigger an alert in a customer service center (CSC) 312. In this embodiment, the CSC 312 acting as a suggested order generator generates a proposed purchase and shipping order to supply a replacement replenishable item 210a to the user. The CSC 312, in turn, may utilize the transmitter portion of the replenishment communication agent 302 to communicate the proposed purchase and shipping order to the medical device 200 for confirmation. Utilizing the CSC 312 provides an opportunity to verify and troubleshoot the replenishment process prior to implementing a fully automated system. In addition, the CSC 312 provides a mechanism by which users that do not have the infrastructure to support a fully automated replenishment system may receive many of the benefits of the fully automated replenishment system 100.

The proposed purchase and/or shipping orders, regardless of how they are generated at the replenishment center 300, may be communicated via the transmitter portion of the replenishment communication agent 302 to: the medical device 200 for acceptance, modification or rejection by the user via the GUI 204c; a laboratory supervisor for approval; an accounting or inventory department; or to any other desired location or individual responsible for the approval and/or ordering of reagents and other replenishable items.

Figure 4:
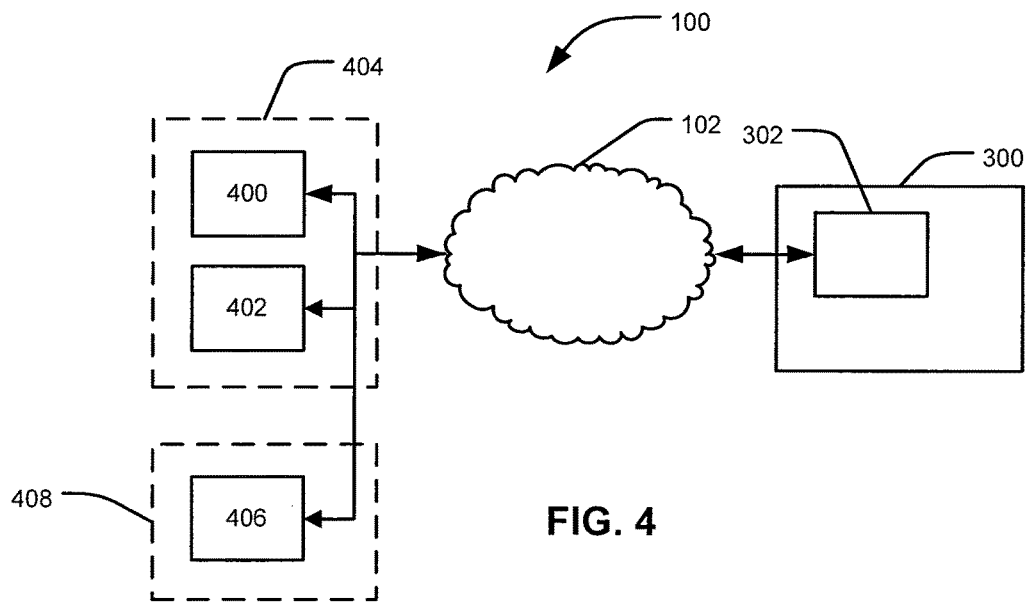
FIG. 4 illustrates an embodiment of a multi-site system for auto-replenishment and monitoring as disclosed herein.
Figure 5:
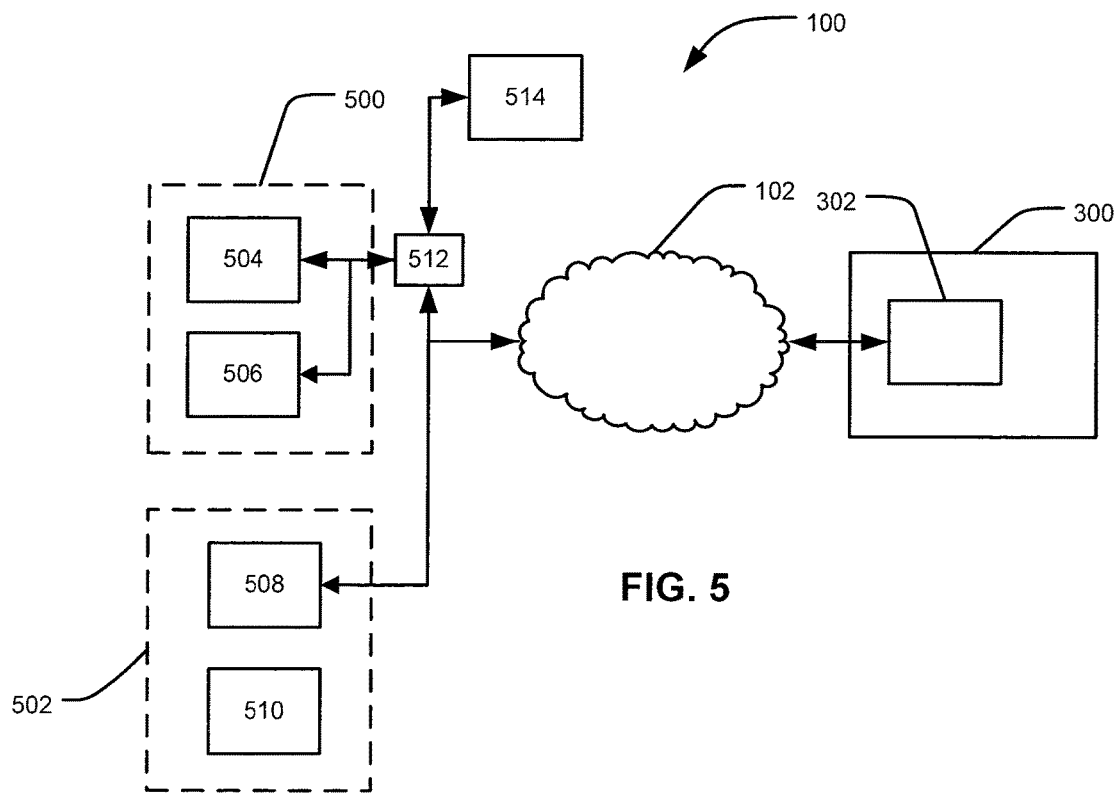
FIG. 5 illustrates another embodiment of the multi-site system for auto-replenishment and monitoring shown in FIG. 4.

FIGS. 4 and 5 illustrate alternate multi-device, multi-location embodiments of the auto-replenishment system 100. FIG. 4 illustrates an embodiment of an auto-replenishment system 100 that includes a client having multiple locations and/or multiple medical devices at each location. In this embodiment, a single contract or service agreement may be established between the replenishment center 300 and the medical devices 400, 402 at a first location 404 and medical device 406 at a second location 408. In this embodiment, the service contract may be stored in the replenishment database 308. The service contract, in turn, may contain and identify each of the medical devices 400, 402 and 406 by, for example, a machine serial number, a unique alias or name, an Internet Protocol (IP) address and/or a location identification. In this way, communications to and from the medical devices 400, 402 and 406 and the replenishment center 300 may specifically be addressed and delivered to a desired recipient.

FIG. 5 illustrates an embodiment of an auto-replenishment system 100 that includes a client having multiple locations and/or multiple medical devices at each location. In this embodiment, multiple contracts or service agreements related to a single client or user may be established between the replenishment center 300 and a first location 500 and a second location 502. The first location 500 may include medical devices 504 and 506 and the second location may include medical devices 508 and 510. In this embodiment, the service contracts may be stored in the replenishment database 308 and may contain different business rules, thresholds and/or requirements for replacing reagents and/or replenishable items. For example, the first service contract associated with the first location 500 and the medical devices 504 and 506 may define a different replenishment threshold than the second service contract because each location may have different consumption rates, different storage capacity for reagents, replenishable items and other consumables, or each location may require different shipping times based on their relative distance from the replenishment center.

FIG. 5 further includes, an alternate embodiment, a router or server 512 that may be configured to intercept and direct communications between the medical devices 504 and 506 and the replenishment center 300. For example, the replenishment center 300 may broadcast a communication to the first location 500 and the router 512 may direct and/or address the communication to one of the intended medical devices 504 and 506. Alternatively, the router 512 may redirect the communication to an accounting terminal 514 or other supervisory system for approval. In an alternate embodiment, the router or server 512 may act as a collection or aggregation point for the medical devices 504 and 506. For example, each of the medical devices 504 and 506 may communicate the cycle count and testing information related to the reagent and other consumable or replenishable item stored in the database 206. The router or server 512 may package, compress or otherwise communicate information related to each of the medical devices 504 and 506 at the first location in a single transmission to the replenishment center 300.

The medical devices 400, 402, 406 and 504 to 510, as used herein, are intended to contain the same capabilities and functions as the medical device 200 discussed above in connection with FIGS. 1 and 2. In other embodiments, each of the medical devices 400, 402, 406 and 504 to 510 may be different types of medical devices, hematology device or other testing instruments.

Figure 6A:
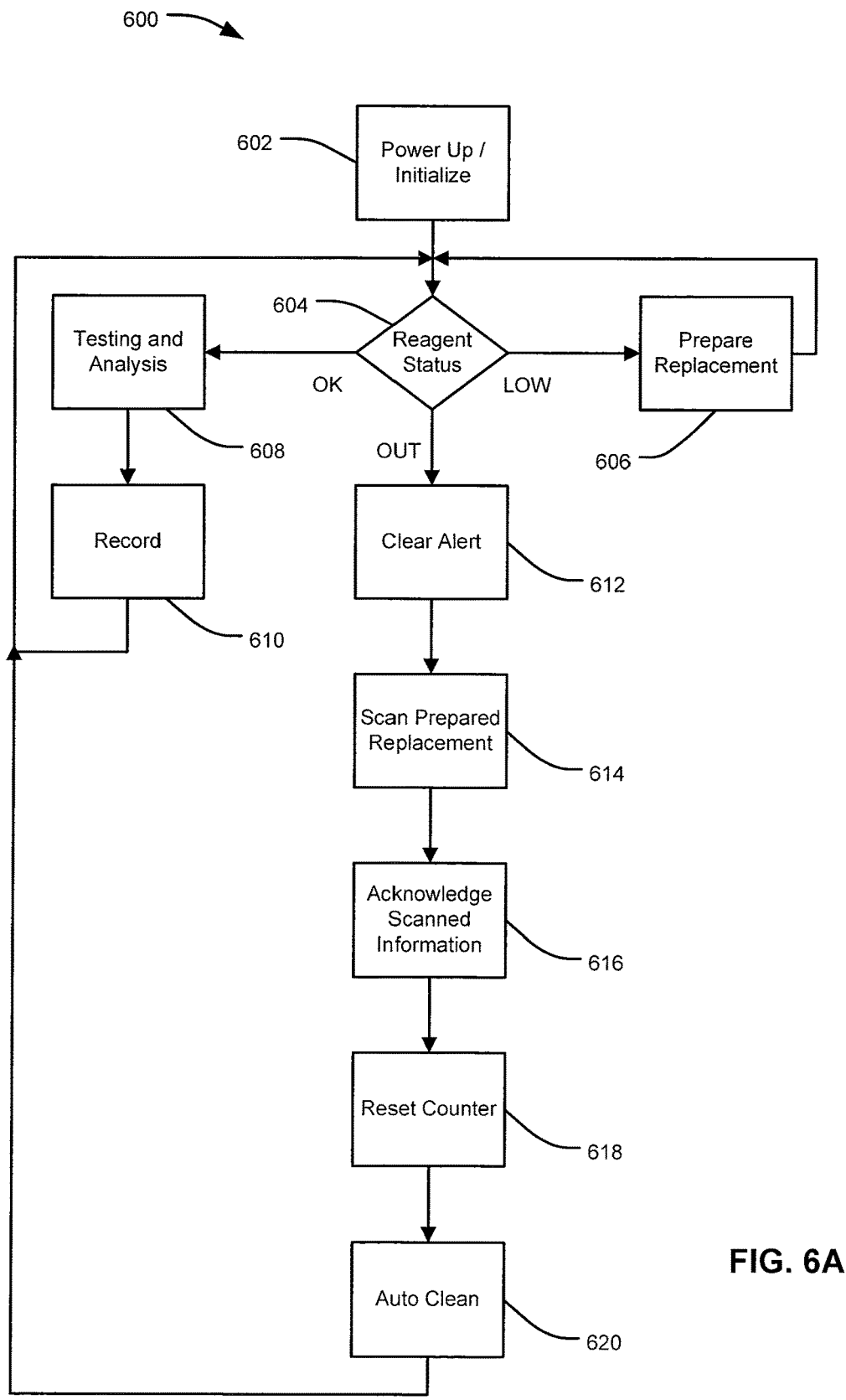
FIG. 6A illustrates an operational flowchart of a medical device configured for operation in an auto-replenishment system.

FIG. 6A illustrates an example of a high level flowchart 600 representative of a normal start up and operational cycle of the medical device 200. At block 602, a user may begin a power-up and initialization routine associated with the medical device 200. The power-up and initialization routine may include a login with a user name and password which may provide access to the functionality of the medical device 200. Moreover, the user name and password may provide or allow access to the communication functionality provided by the device communication agent 202 and the communication link 102. In this way, a user may be allowed access to the Internet, other networked equipment and resources. The power-up and initialization routine may include mechanical and software checks intended to place the medical device 200 in operational condition.

At block 604, the status of the reagents and other replenishable items 210a to 210d can be determined. For example, the medical device 200 may automatically weigh or otherwise measure the reagents and other replenishable items 210a to 210d. Alternatively, the user may visually inspect or evaluate the reagents and other replenishable items 210a to 210d.

At block 606, one or more of the reagents and other replenishable items 210a to 210d has been determined, either automatically or manually, to be low or near exhaustion. A replacement reagent and/or other replenishable item (s) 210a to 210d may be requested from a local or off-site supply depot or storage and prepared for use when the corresponding reagent or replenishable item is completely exhausted. Once the replacement reagent or replenishable item is prepared and ready for eventual use, the process returns to block 604.

At block 608, the reagents and other replenishable items 210a to 210d has been determined, either automatically or manually, to be ready for operation. The analysis subsystem 200b, and more particularly the analysis module 212, performs the instructed analysis, testing and/or cleaning cycles. The analysis module 212 may access reagent and/or replenishable item information in database 206 as shown by way of example in Table 1. The first two columns of Table 1 provide the complete name and an abbreviation for each of the reagents and/or replenishable items, respectively. The third column provides an approximate number of cycles and/or tests which may be expected from a given known reagent and/or replenishable item. The fourth column provides the size and/or volume of each container of reagent and/or replenishable item.

TABLE 1

Approximate number of cycles per particular reagent, which may be run by the medical device 200.

| Replenishable Item | Abbreviation | # of cycles per container | Capacity per container |
|---|---|---|---|
| Cellpack | EPK | Approx. 660 | 20.0 L |
| Cellsheath | ESE | Approx. 7300 | 20.0 L |
| Stromatolyser-FB | FBA | Approx. 2750 | 5.0 L |
| Stromatolyser-4DL | FFD | Approx. 2750 | 5.0 L |
| Stromatolyser-4DS | FFS | Approx. 200 | 42 mL |
| Stromatolyser-NR(L) | SNR | Approx. 2000 | 3.6 L |
| Stromatolyser-NR(S) | SNR | Approx. 2000 | 43 mL |
| Sulfolyser | SLS | Approx. 10000 | 5.0 L |
| Stromatolyser-IM | SIM | Approx. 3200 | 10.0 L |
| Ret. Search (II)-(Diluent) | RED | Approx. 550 | 1.0 L |
| Ret. Search (II) - (Die solution) | RED | Approx. 550 | 12 mL |

Based, at least in part, on the information represented in Table 1, the analysis module 212 may cooperate with the database 206 and the tracking module 208 to generate a cycle count analysis. Alternatively, the cycle count analysis may be performed at the auto-replenishment module 306 utilizing the inventory calculator. Table 2 illustrates an exemplary cycle count analysis that details cycle test versus reportable test count generated and provided by the analysis module 212. The first column of Table 2 indicates the tests or procedures that may be performed by the medical device 200. The second through the fifth columns break down the cycle count associated with a medical device 200 into different count categories. For example, the second list the approximate number of cycles that can be conducted before a given reagent or other consumable item is depleted. The third column lists the approximate number of rerun or retests that may be conducted by the medical device 200 during testing of various patient samples. The fourth column indicates the number of quality control, cleaning and or maintenance cycles that may be conducted by the medical device 200 during testing of various patient samples. The sixth column provides a total of the preceding three columns while the seventh column lists the total number of cycles that may be reported for the purposes of replenishment. In other words, to analyze six hundred patient samples, it may be necessary to conduct six hundred and sixty cycles.

TABLE 2

Cycle count versus reportable test count

| | Cycle Count | | | | |
|---|---|---|---|---|---|
| Test | Order | Rerun | QC | Total | Reportable |
| 1 | 600 | 50 | 10 | 660 | 600 |
| 2 | 500 | 45 | 10 | 555 | 500 |
| 3 | 100 | 5 | 5 | 110 | 100 |
| 4 | 150 | 10 | 5 | 165 | 150 |
| Total | 1350 | 110 | 30 | 1490 | 1350 |

At block 610, the analysis module 212 and tracking module 208 may cooperate with the control module 204 and database 206 to determine reagent and replenishable item utilization. For example, because the amount of each reagent or other replenishment item used for each given test is known and fixed, because the number of test, maintenance and/or cleaning cycles is known and record, the quantity of reagent and replenishable item utilized may be determined and compared to capacity per container (see Table 1). Once programmed tests and analysis have been completed by the medical device 200, and the reagent and/or replenishable item status is determined, stored and reported, the process returns to block 604.

If one or more of the reagents and other replenishable items 210a to 210d has been determined, either automatically or manually, at block 604 to be exhausted, the process moves to block 612. If the exhausted replenishable item its determined automatically, the control module 204 and GUI 204c may display an alert. At this point the user of the medical device 200 may clear or otherwise acknowledge the alert. The alert may further signify a shutdown or pause in any ongoing analysis or test conducted by the analysis module 212. In another embodiment, the alert may trigger or otherwise initiate a communication or update to the database 206 and/or the replenishment center 300 via the communication link 102.

At block 614, the user may retrieve the previously prepared replacement reagent and/or replacement item discussed in connection with block 606. However, should this be the first indication or a depleted reagent and/or replenishable item, the user may be required to retrieve a replacement from a stock room or other storage location. The replacement reagent may be scanned for use via the scanner 208a.

At block 616, the information retrieved via the scanner 208a may be displayed via the GUI 204c for verification, communicated to the database 206 for storage and/or communicated to the replenishment center 300.

At block 618, the cycle counter may be reset to zero (0) with respect to the replaced reagent or replenishable item. The resetting process may be accomplished automatically via a user input received and processed via, for example, the GUI 204c. Alternatively, the resetting process may be triggered or initiated by the action of scanning the replacement or clearing the alert.

At block 620, an automatic or auto-cleaning function may be initiated. The auto-clean function may include preparing or priming the medical device with replacement reagent or other replenishable item loaded thereon. Alternatively, the auto-clean function may include the analysis module 212 and include preparing the included subsystems for operation. Once resupply operation has been completed and the medical device 200 is once again fully operational, and the reagent and/or replenishable item status is determine, stored and reported, the process returns to block 604.

Figure 6B:
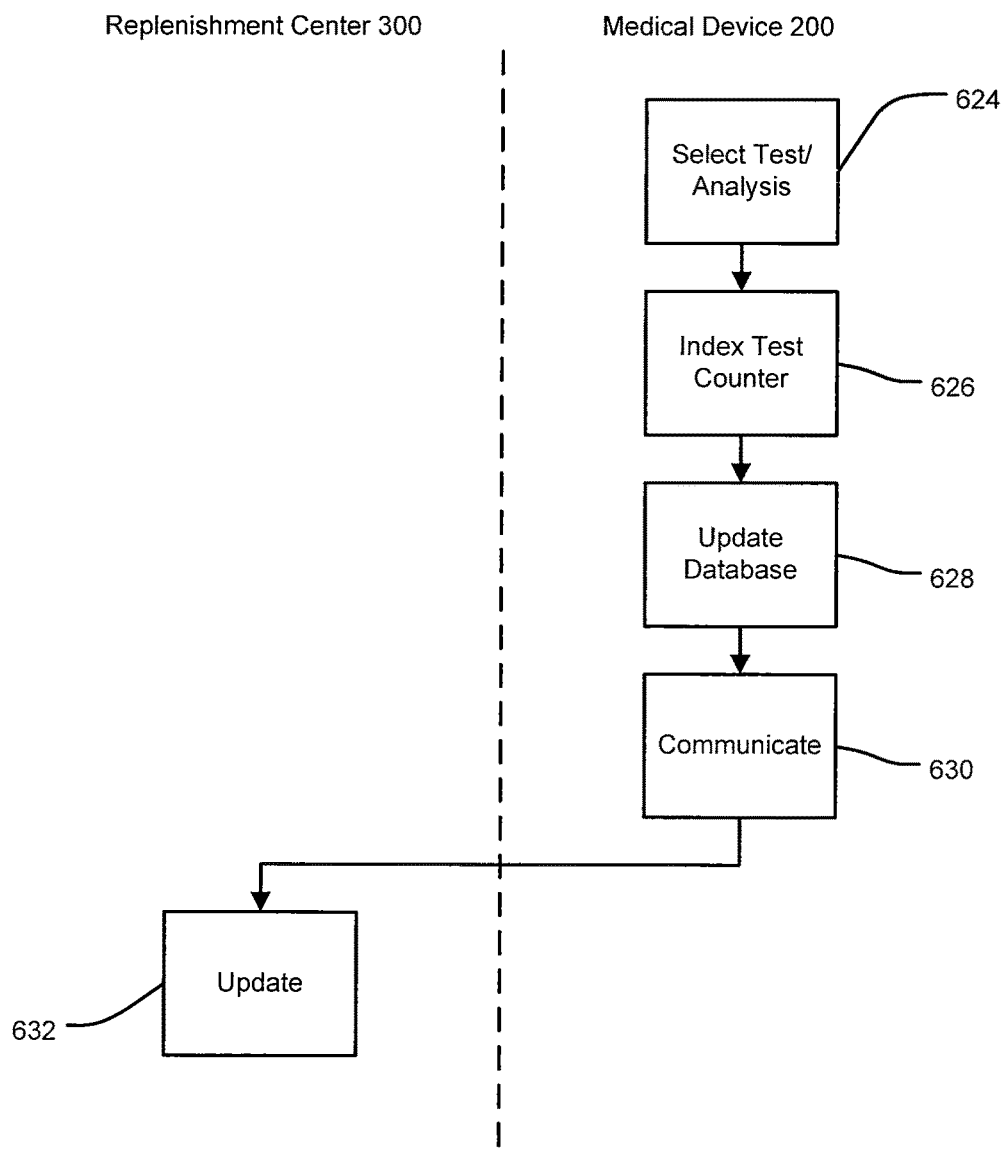
FIG. 6B illustrates an operational flowchart detailing an information update between a medical device and an auto-replenishment center.

FIG. 6B illustrates an exemplary communication and update process between the medical device 200 and the replenishment center 300.

At block 624, the user may interact with the GUI 204c to identify and select one or more tests and/or analyses to be performed on a patient sample. In response to a user command, the medical device 200 executes and performs one or more analysis processes on the patient sample.

At block 626, the medical device 200 may index and update a test or maintenance counter detailing the type of tests performed in response to the user's selection(s).

At block 628, the analysis module 212 and/or the tracking module 208 of the medical device 200 may update and store the updated test counter information in the database 206. The updated test counter information may include a time stamp to allow creation of a time based history file or record within the database 206. The history file may in turn be utilized to predict usage patterns for the medical device 200. Alternatively, the updated test counter information may be stored at a specific memory location within the database 206 such that it overwrites any previously stored test counter information. The updated test counter information may, in another embodiment, be combined or augmented with any or all of the correlated data stored within the database 206.

At block 630, the updated test counter information may be communicated from the database 206 to the transmitter portion of the device communication agent 202 and the communication link 102.

At block 632, the updated test counter information may be received by the receiver portion of the auto-replenishment communication agent 302. The received test counter or operation information may, in turn, be utilized by the inventory calculator portion of the auto-replenishment module 306 and/or the record updater portion of auto-replenishment database 308 of to the replenishment center 300.

Figure 6C:
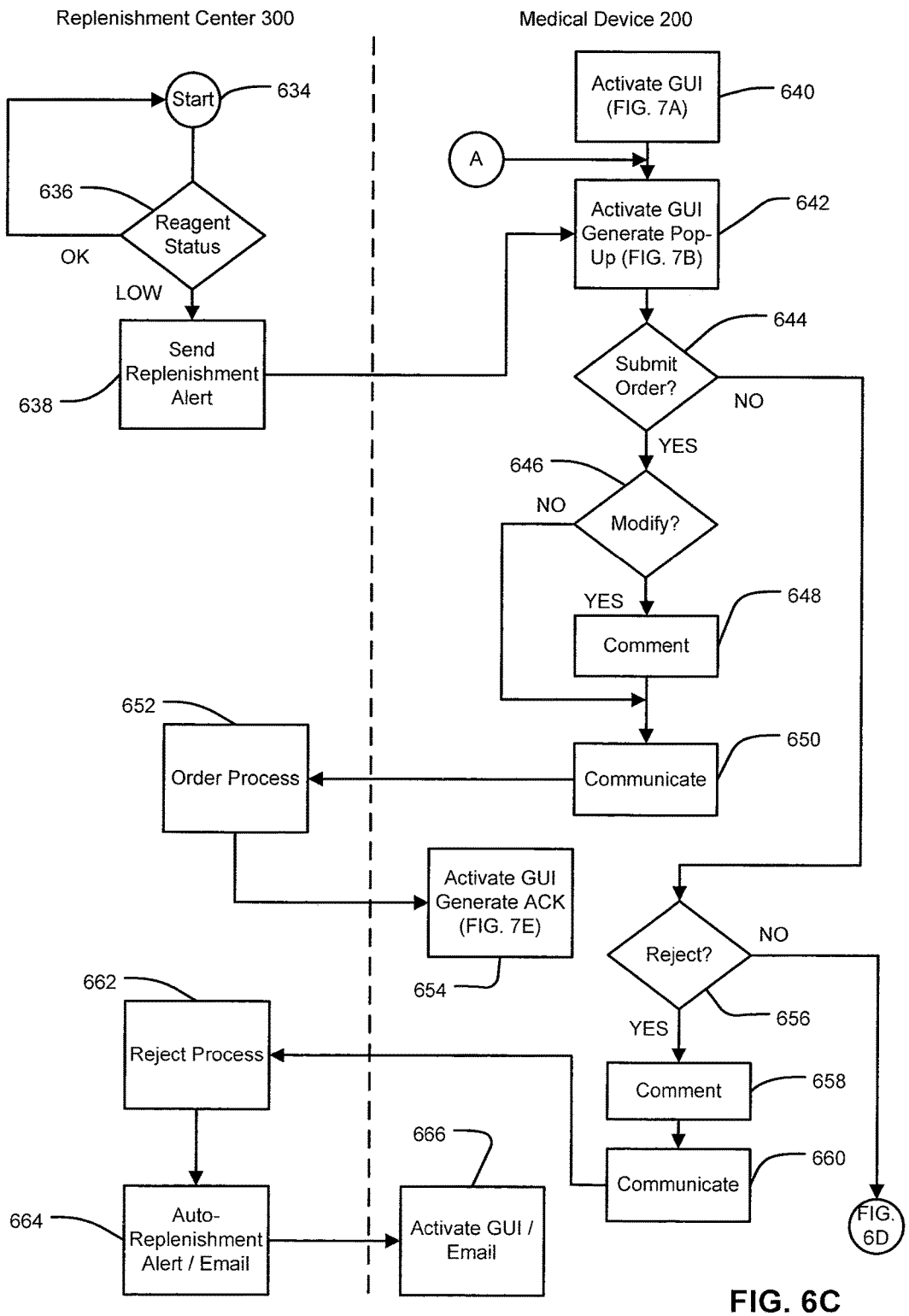
FIGS. 6C and 6D illustrate replenishment and monitoring operational flowcharts that may be utilized in connection with an exemplary auto-replenishment system.
Figure 6D:
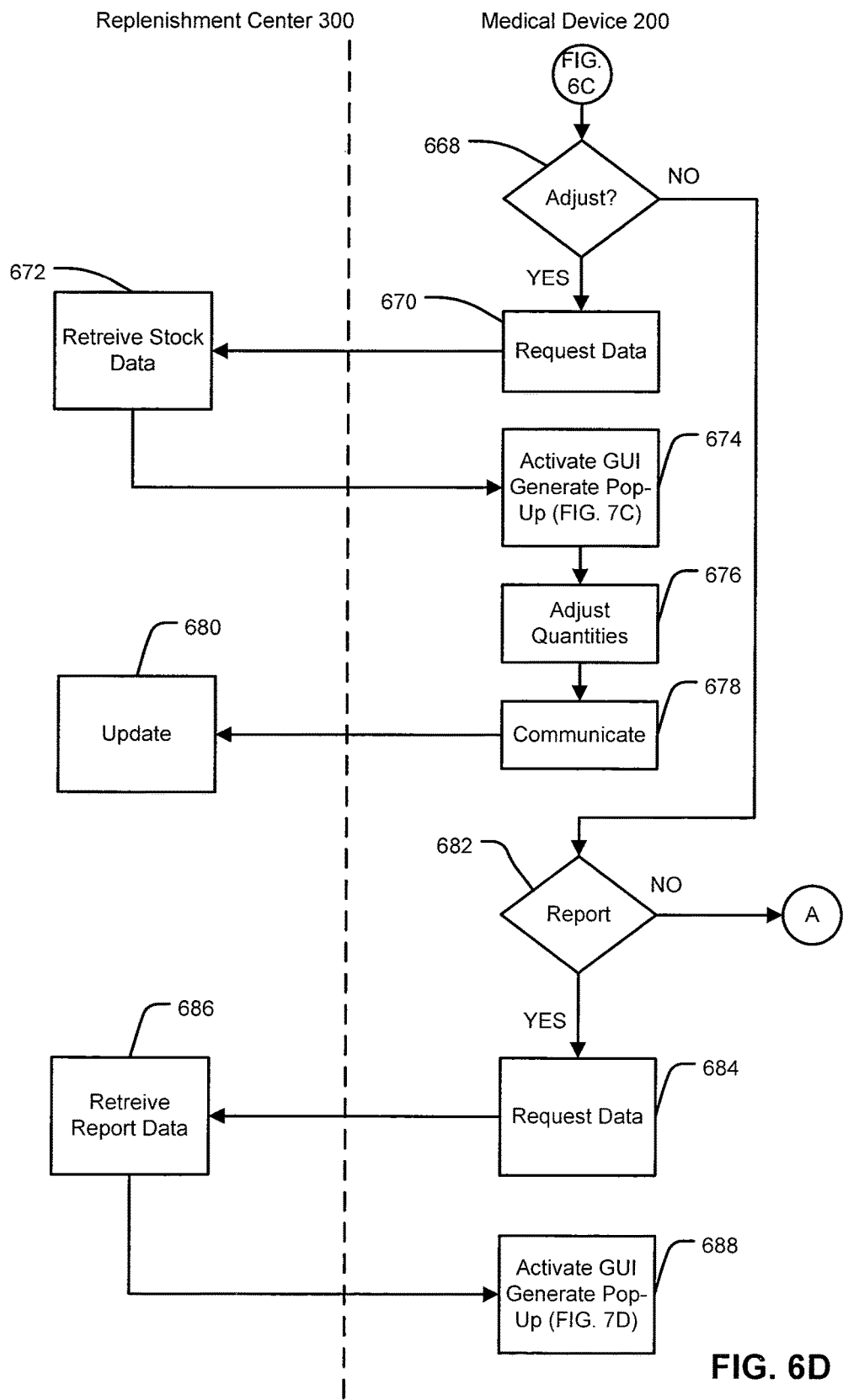

FIGS. 6C and 6D illustrate exemplary interactions between the medical device 200 and the auto-replenishment center 300 during a manual and/or automatic replenishment operation. At block 634, the replenishment center 300 may manually or automatically, according to a pre-determined schedule, begin utilizing the inventory calculator to perform a replenishment analysis for one or more medical devices. For example, a timed schedule may be established that results in the replenishment analysis being conducted every twenty-four (24) hours. Alternatively, the replenishment analysis may be initiated manually by the replenishment center.

Figure 7A:
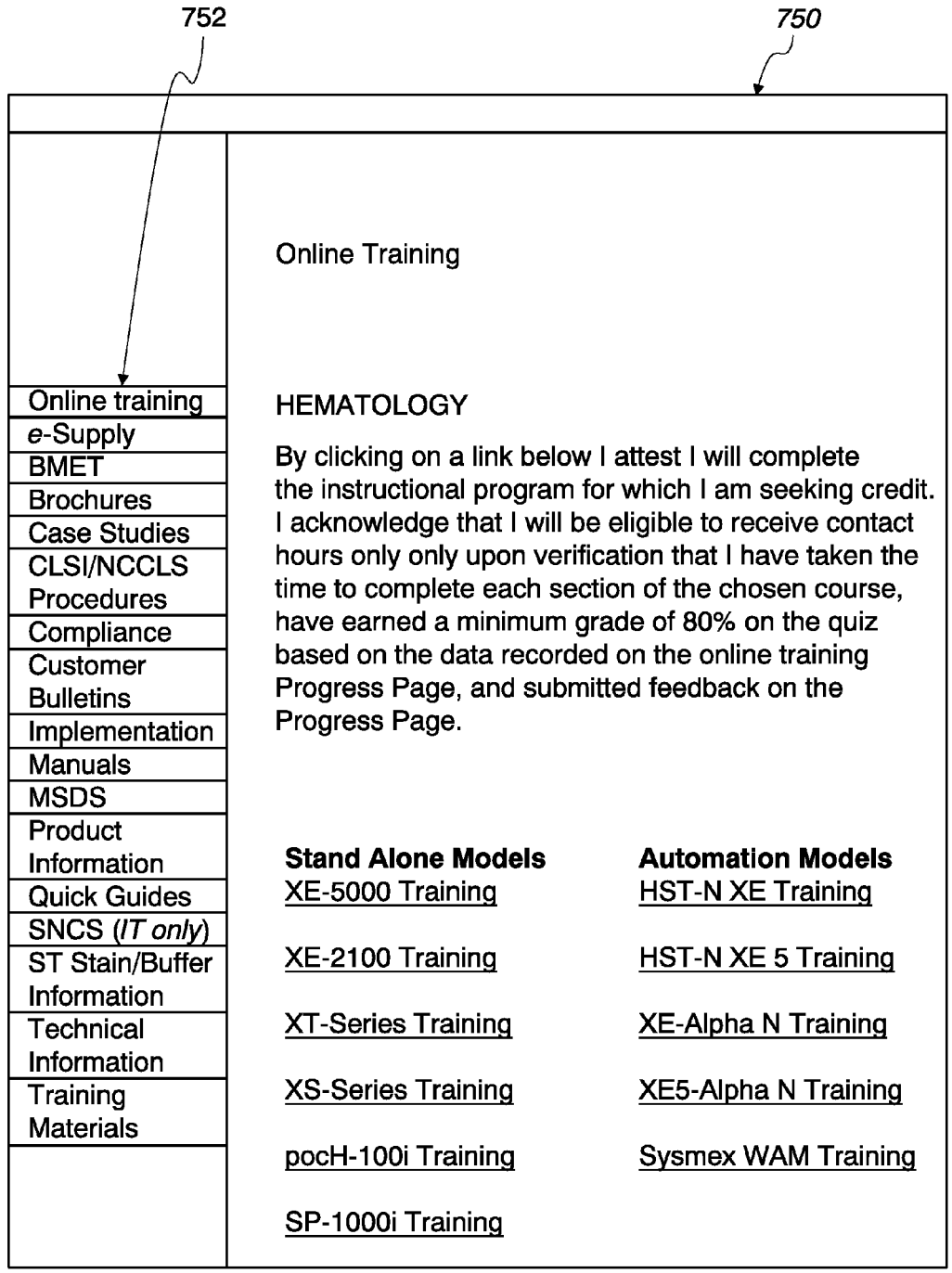

Alternatively, at block 640, the user of the medical device 200 may manually initiate the replenishment process by accessing, either via the medical device itself or an Internet website, an e-supply menu screen 750 (see FIG. 7A).

At block 636, the auto-replenishment module 306 may access and evaluate the updated test counter information provided at block 632 of FIG. 6B. For example, the auto-replenishment module 306 may utilize the inventor calculator to calculate the reagent 210a remaining based on the difference between the initial amount of reagent (see Table 1) and the number and type of tests performed (see Table 2). The remaining amount of reagent may be compared to a threshold to determine if resupply is in order. In one embodiment, the threshold may be fifty percent (50%) of, for example, the total number of replenishable item boxes in inventory and/or the initial volume of a reagent or replenishable item. In another embodiment, the threshold may be dynamically calculated based on the history file and delivery time associated with replacement order. If the remaining reagent exceeds the threshold, the process may terminate and return to block 634 to await the next scheduled or manual activation.

If the inventory calculator that performs the replenishment analysis determines that the remaining amount of a replenishable item is less than the threshold, then at block 638, the auto-replenishment module 306 may determine that the remaining reagent is below the threshold thereby triggering a replenishment alert to be generated by an alert sender portion of the replenishment communication agent 302. The replenishment alert generated by the alert sender may be communicated via the transmitter portion of the replenishment communication agent 302 to the GUI 204c of the medical device 200. Alternatively, the replenishment alert generated by an alert sender portion of the replenishment communication agent 302 may be an email alert containing a link to the e-supply menu screen 750 shown in FIG. 7A.

At block 642, the e-supply menu screen 750 and/or the replenishment alert provides access, via the GUI 204c, to a replenishment order screen shown in FIG. 7B. In this example, it will be assumed for clarity that the replenishment order screen shown in FIG. 7B is accessed by the replenishment alert generated by the alert sender discussed above. The replenishment alert may identify the reagent or other replenishable item determined to need replacement (in this example the reagent 210a), may suggest a replacement amount and/or may identify the stock levels as determined by the auto-replenishment module 306. The replenishment alert may provide the ACCEPT, REJECT and MODIFY functionality discussed in connection with FIGS. 7A to 7E.

At block 644, the user may interact with the GUI 204c to accept the proposed purchase order via the SUBMIT button 710.

At block 646, prior to final acceptance and submission of the proposed purchase order delivered via the replenishment alert, the user may modify the proposed or recommended quantity. The proposed or recommended quantity may be determined by one or more business rules stored by the auto-replenishment database 308. For example, the auto-replenishment database 308 may store previous orders and based on usage or consumption patterns attempt to predict and recommend the proposed resupply amount. Alternatively, the auto-replenishment database 308 may store a fixed resupply amount based on stock and/or usage level desired by the user.

At block 648, if the user has decided to modify the proposed or recommended quantity, the user has a further opportunity to provide comments, instructions and/or other information during the acceptance/submission process.

At block 650, the information gathered via the proposed and/or modified purchase order may be communicated via the transmitter portion of the device communication agent 202 to the replenishment center 300.

At block 652, the information received by the receiver portion of the replenishment communication agent 302 at the replenishment center 300 may be utilized by the auto-replenishment module 306 to process and complete the proposed replenishment order.

At block 654, an acknowledgement message or receipt may be transmitted or communicated from the replenishment center 300 to the medical device 200. The acknowledgement message or receipt may be displayed by the GUI 204c as an order confirmation screen 760 (see FIG. 7E). Alternatively, the acknowledgement message may be delivered to one or more email clients designated by the user.

If the user at block 644 does not submit or accept the proposed replenishment order, then at block 656 the user has the opportunity to reject the proposed purchase order.

At block 658, if the user has decided to reject the proposed or recommended quantity, the user has an opportunity to provide comments, instructions and/or other information. The provided comments may serve to modify future proposed purchase orders, modify delivery instructions and/or provide any addition information deemed important by the user.

At block 660, the order rejection information may be communicated via the transmitter portion of the device communication agent 202 to the replenishment center 300.

At block 662, the rejection information received at the replenishment center 300 may be utilized by the auto-replenishment module 306 to update the information stored in the auto-replenishment database 308.

At block 664, a secondary replenishment alert may be established or generated by the alert sender to act as a reminder or backup. The secondary replenishment alert may be emailed or otherwise transmitted to the medical device 200 after, for example, a proscribed period of time (e.g., a day, a week, etc.), a predefined increase in the test counter, the remaining reagent volume falls below a second threshold that is less than the first threshold.

At block 666, the secondary replenishment alert may be delivered to the receiver portion of the device communication agent 202 of the medical device 200. The secondary replenishment alert may be received via an email client or displayed via the GUI 204c.

If at block 656 the user does not reject the proposed replenishment purchase order, then at block 668, the stock quantities stored at the replenishment center 300 may be evaluated and updated.

At block 670, a request for stock information made be generated and communicated to the replenishment center 300.

At block 672, the received stock information request may cause the auto-replenishment module 306, the auto-replenishment database 308 and/or the ERP 310 to package and communicate the requested information.

At block 674, the requested information is delivered to the medical device and displayed via the GUI 204c. In particular, the received information may be formatted and displayed as shown in FIG. 7C.

At block 676, the user may interact with the GUI 204c to adjust or otherwise change the stock quantities stored at the replenishment center 300.

At block 678, the updated quantity information may be communicated via the transmitter portion of the device communication agent 202 to receiver portion of the replenishment communication agent 302 of the replenishment center 300.

At block 680, the stock information stored at auto-replenishment module 306, the auto-replenishment database 308 and/or the ERP 310 may be updated utilizing the record adjuster to reflected to information provided by the user.

If at block 668 the user does not modify or adjust the stock quantities stored at the replenishment center 300, then at block 682, a report detailing current and past replenishment orders may be requested and generated.

At block 684, a request for report information made be generated and communicated to the replenishment center 300.

At block 686, the received report information request may cause the auto-replenishment module 306, the auto-replenishment database 308 and/or the ERP 310 to package and communicate the requested information.

At block 688, the requested information is delivered to the medical device and displayed via the GUI 204c. In particular, the received information may be formatted and displayed as shown in FIG. 7D.

If, at block 682, a report request is not generated, the process may continue and/or return to block 642 and await further commands.

FIGS. 7A to 7E illustrate auto-replenishment interface screens that may be presented via the GUI 204c. FIG. 7A illustrates an e-supply menu screen 750 that may be accessed by the user. For example, the user may interact with the GUI 204c and an e-supply link 752 to access the functionality provided by the replenishment center 300. Alternatively, the user may selected an active link or hyperlink embedded within the secondary replenishment alert to access the e-supply menu screen 750. For example, by selecting the hyperlink, the user may be directed to a secure webpage hosted by the replenishment center 300.

FIG. 7B illustrates a review screen 700 which may be generated at and provided by the replenishment center 300 in response to the combined and correlated data received from the medical device 300. In an alternate embodiment, the review screen may be generated at the medical device 200 and communicated to the replenishment center 300. The review screen 700 may include a part number 702 or stock keeping unit (SKU) and a name 704 identifying each of the reagents, consumables and/or replacement items.

The review screen 700 may further include a recommended quantity 706 that may be supplied and specified by the business rules stored and implemented by the auto-replenishment database 308 and the auto-replenishment module 306, respectively. The recommended quantity business rule could, in another embodiment, be stored and implemented by a local accounting department, ERP or stored in the database 206. THE recommended quantity could be determined based on past order and/or usage patterns, known or calculated consumption rates and/or fixed amounts requested by the user.

The review screw 700 may further include an actual quantity 708 which may be adjusted or modified manually. A "SUBMIT" button 710 allows the user to confirm the order can initiate communication of the same to the replenishment center 300 for fulfillment. Alternatively, a "REJECT" button 712 allows the user to reject the recommended or provided order.

FIG. 7C illustrates a stock screen 714 which may be presented via the GUI 204c. As previously described, the stock screen 714 may include the part number 702 and the name 704 of a given reagent or replenishable item available or accessible to the medical device 200. The stock screen 714 may further provide a manufacturing lot number 716 and/or an expiration date 718 for each listed item. The stock screen 714 may further provide a stock amount 720 that reflects the quantity of an item available to the medical device 200 as reflected by data stored at the replenishment center 300. Thus for an item reflecting a stock amount 720 of one (1), the records kept at the replenishment center 300 relating to the medical device 200 indicate that a replacement item is available. Available items may be items or parts stored locally (e.g., within the laboratory), stored in a common facility that serves multiple laboratories or an item that may be delivered quickly, and without expedited costs, from a supply depot or warehouse. If the records of the replenishment center 300 are inaccurate for any reason, the user of the medical device may update/correct the information and submit the same to the replacement center via the SUBMIT button 710.

FIG. 7D illustrates a tracking screen 722 that may be provided via the GUI 204c. The tracking screen 722 may include an order identifier 724 as well as a purchase order number 726 associated with a given order. The tracking screen 722 may include a shipping status 728 (e.g., in process, shipped, delivered, alert) as well as tracking information 730 provided by, for example, a shipper or carrier. The tracking screen 722 may further include the name and/or time stamp 732 necessary to identify anyone that changes, accepts or rejects a recommended or pending order. In this way, the auto-replenishment system 100 provides a mechanism to track users of the medical device 200 as well as utilization of the reagents and other replenishable items.

Figure 7E:
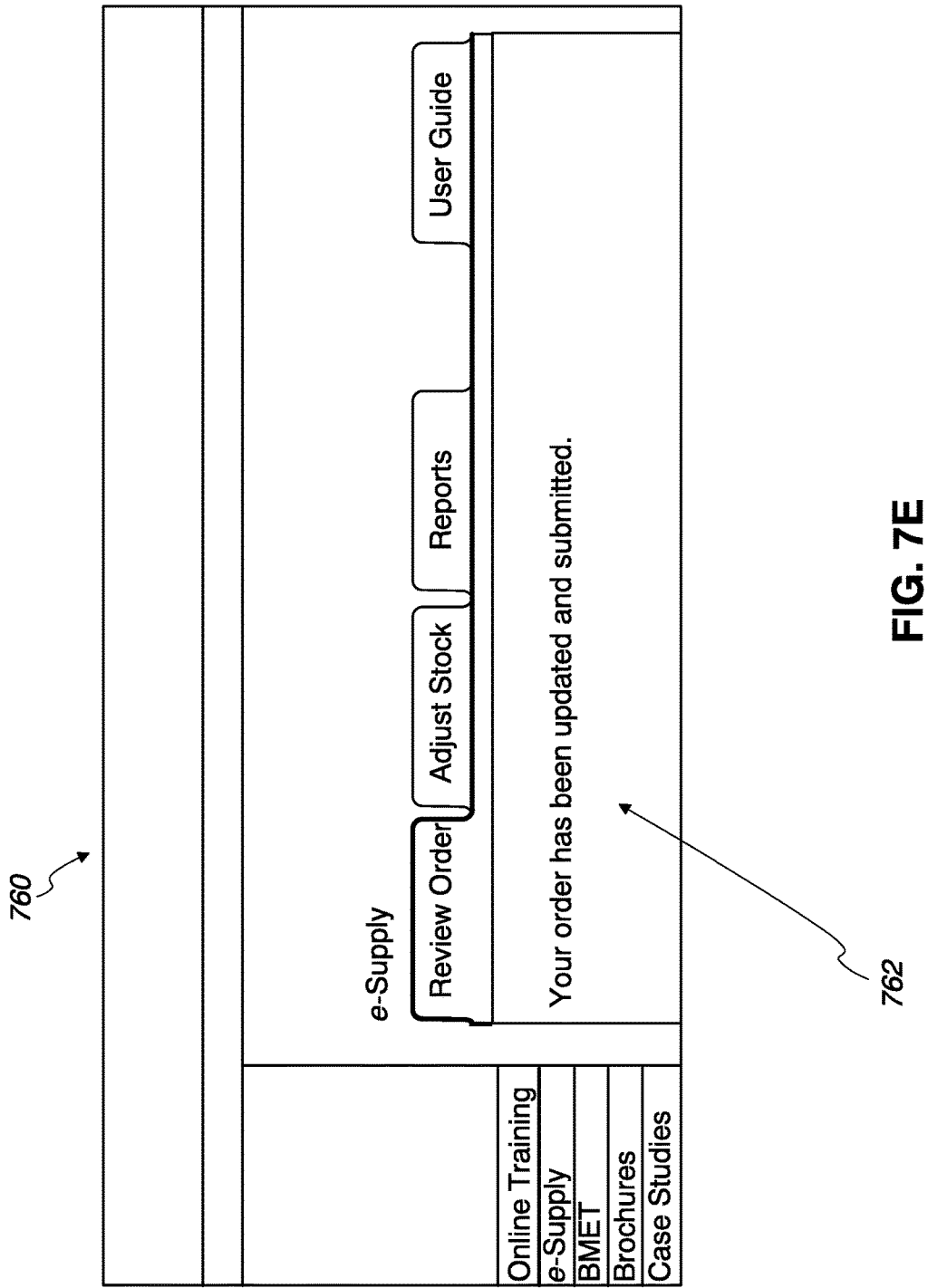

FIG. 7E illustrates an order confirmation screen 760 or receipt which may be provided to the user via the GUI 204c. For example, upon submission of a modified, unmodified or rejected order, the replenishment center 300 may communicate a confirmation message 762 to acknowledge receipt of the instructions provided by the user.

The information provided via the screens 700, 714, 722, 750 and 760 may, in other embodiments, be directed to an accounting or purchasing department, a supervisors work station or to a different medical device identified by the replenishment center 300. Alternatively, the information may be provided as a receipt or confirmation where orders are fulfilled automatically, based on business rules such as, minimum order quantity, maximum purchase amount or limit, one or more timing constraints, etc.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. A method for soliciting an order of a reagent from a plurality of medical diagnostic analyzer systems each comprising at least one analyzer module which performs medical diagnostic analysis using a reagent, the method comprising:
   receiving a number of analyses cycles performed by at least one of the plurality of medical diagnostic analyzer systems from the at least one of the plurality of medical diagnostic analyzer systems;
   recording in a database the number of analyses cycles in relation to the at least one of the plurality of medical diagnostic analyzer systems;
   calculating and storing in the database a remaining quantity of inventory of the reagent kept for the at least one of the plurality of medical diagnostic analyzer systems based on the number of analyses cycles recorded in the database;
   determining, for reagents having less than a predetermined threshold defined as a predetermined percentage of an initial inventory of the reagent, a recommended quantity of the reagent to be ordered based on at least one of a past order history of a user of the at least one of the plurality of medical diagnostic analyzer systems and a consumption rate of the reagent;
   displaying generating, at the at least one of the plurality of medical diagnostic analyzer systems, for the reagents having less than the predetermined threshold, a screen comprising a suggested order of the recommended quantity of the reagent with an option of accepting or rejecting the suggested order, the screen also providing access to information on at least lot expiration dates of the reagents kept in the inventory,
   receiving from the at least one of the plurality of medical diagnostic analyzer systems a user modification to the suggested order via the screen.

2. A method for giving a user of a medical diagnostic analyzer system an option on an order for a reagent used in the medical diagnostic analyzer system, comprising:
   utilizing a reagent during the analysis of a sample by an analysis apparatus;
   determining a number of analyses cycles performed by the analysis apparatus;
   transmitting the number of analyses cycles performed by the analysis apparatus to a replenishment center;
   receiving a suggested order for ordering the reagent from the replenishment center;
   displaying, based on the received suggested order, a screen including a recommended quantity of the reagent to be ordered by the user of the medical diagnostic analyzer system simultaneously with an option of accepting or rejecting the suggested order, the screen also providing an access to information on at least lot expiration dates of the reagents kept in an inventory; and
   receiving from the medical diagnostic analyzer system a user modification to the suggested order via the screen.

3. The method according to claim 1, further comprising sending an alert to the user when the calculated remaining quantity becomes less than the predetermined threshold.

4. The method according to claim 3, wherein the alert directs the user to access the suggested order via a network.

5. The method according to claim 1, further comprising presenting the remaining quantity of the inventory of the reagent recorded in the database for correction by the user to accord with the remaining quantity of the inventory of the reagent kept by the user.

6. The method according to claim 1, further comprising showing a history of orders placed by the user, in response to a request from the user.

7. The method according to claim 2, further comprising sending an alert to the user when the calculated remaining quantity becomes less than the predetermined threshold.

8. The method according to claim 7, wherein the alert directs the user to access the suggested order via a network.

9. The method according to claim 2, further comprising presenting the remaining quantity of the inventory of the reagent recorded in the database for correction by the user to accord with the remaining quantity of the inventory of the reagent kept by the user.

10. The method according to claim 2, further comprising showing a history of orders placed by the user, in response to a request from the user.

11. A method for soliciting an order of a reagent from a plurality of medical diagnostic analyzer systems each comprising at least one analyzer module which performs medical diagnostic analysis using a reagent, the method comprising:
   receiving a number of analyses cycles performed by at least one of the plurality of medical diagnostic analyzer systems from the at least one of the plurality of medical diagnostic analyzer systems;
   recording in a database the number of analyses cycles in relation to the at least one of the plurality of medical diagnostic analyzer systems;
   calculating and storing in the database a remaining quantity of inventory of the reagent kept for the at least one of the plurality of medical diagnostic analyzer systems based on the number of analyses cycles recorded in the database;
   determining, for reagents having a remaining quantity of the reagent that is less than a predetermined threshold calculated based on at least one of a history file of order and a delivery time, a recommended quantity of the reagent to be ordered based on at least one of a past order history of a user of the at least one of the plurality of medical diagnostic analyzer systems and a consumption rate of the reagent;
   generating, for the reagents having a remaining quantity of the reagent less than the predetermined threshold, a suggested order programmed to give the user the recommended quantity of the reagent simultaneously with an option of accepting or rejecting the suggested order,
   transmitting to the at least one of the plurality of medical diagnostic analyzer systems the suggested order, and displaying a screen showing the suggested order including at least lot expiration dates of the reagents in the inventory, receiving from the at least one of the plurality of medical diagnostic analyzer systems a user modification to the suggested order via the screen.

12. The method according to claim 1, wherein the screen provides for user modification including a request to order additional reagent via the screen for reagents used by the at least one analyzer module that are depleted.

13. The method according to claim 2, wherein the screen further shows an inventory of a reagent used by the medical diagnostic analyzer system.

14. The method according to claim 11, wherein, the screen provides for user modification including a request to order additional reagent via the screen for reagents used by the at least one analyzer module that are depleted.

15. The method of according to claim 1, wherein the screen further provides an access to information on a remaining quantity of the reagents in association with respective lot expiration dates.

16. The method of according to claim 2, wherein the screen further provides an access to information on a remaining quantity of the reagents in association with respective lot expiration dates.

17. The method of according to claim 11, wherein the screen further provides an access to information on a remaining quantity of the reagents in association with respective lot expiration dates.

* * * * *

UNITED STATES PATENT AND TRADEMARK OFFICE
CERTIFICATE OF CORRECTION

PATENT NO. : 10,837,974 B2
APPLICATION NO. : 12/750386
DATED : November 17, 2020
INVENTOR(S) : Stephen J. Postma et al.

Page 1 of 1

It is certified that error appears in the above-identified patent and that said Letters Patent is hereby corrected as shown below:

In the Claims

In Column 17, Claim 1, Line 44, delete "generating".

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*